United States Patent [19]

Korkolainen et al.

[11] Patent Number: 5,489,614
[45] Date of Patent: Feb. 6, 1996

[54] CATECHOL DERIVATIVES, THEIR PHYSIOLOGICALLY ACCEPTABLE SALTS, ESTERS AND USE

[75] Inventors: Tapio J. Korkolainen, Helsinki; Erkki A. O. Nissinen, Espoo; Reijo J. Bäckström, Helsinki; Aino K. Pippuri, Espoo, all of Finland

[73] Assignee: Orion-yhtyma Oy, Espoo, Finland

[21] Appl. No.: 461,752

[22] Filed: Jun. 5, 1995

Related U.S. Application Data

[63] Continuation of Ser. No. 294,762, Aug. 23, 1994, abandoned, which is a continuation of Ser. No. 658,666, Feb. 21, 1991, abandoned, which is a continuation-in-part of Ser. No. 288,979, Dec. 23, 1988, Pat. No. 5,001,152, which is a continuation-in-part of Ser. No. 587,791, Sep. 25, 1990, Pat. No. 5,112,861, which is a division of Ser. No. 126,911, Nov. 27, 1987, Pat. No. 4,963,590.

[30] Foreign Application Priority Data

Feb. 27, 1990 [GB] United Kingdom .................. 9004348

[51] Int. Cl.$^6$ ........................................ A61K 31/12
[52] U.S. Cl. ........................ 514/676; 514/678; 514/689
[58] Field of Search ............................ 514/689, 678, 514/676

[56] References Cited

U.S. PATENT DOCUMENTS

| | | | |
|---|---|---|---|
| 3,804,904 | 4/1974 | Bentley et al. | 260/607 |
| 3,886,285 | 5/1975 | Bentley et al. | 424/333 |
| 4,618,627 | 10/1986 | Murase et al. | 514/678 |

FOREIGN PATENT DOCUMENTS

| | | | |
|---|---|---|---|
| 0081321 | 11/1982 | European Pat. Off. | |
| 0012939 | 1/1983 | European Pat. Off. | C07C 45/36 |
| 0044260 | 4/1984 | European Pat. Off. | C07C 47/565 |
| 0125919 | 6/1984 | European Pat. Off. | |
| 0155335 | 9/1985 | European Pat. Off. | C07C 45/71 |
| 0149407 | 4/1987 | European Pat. Off. | |
| 0149952 | 7/1987 | European Pat. Off. | |
| 237929 | 11/1987 | European Pat. Off. | |
| 0326379 | 1/1989 | European Pat. Off. | |
| 902586 | 11/1960 | United Kingdom. | |
| 1188364 | 5/1968 | United Kingdom. | |
| 1276966 | 11/1970 | United Kingdom. | |
| 2008103 | 10/1978 | United Kingdom. | |
| 2198128 | 6/1988 | United Kingdom | C07C 121/75 |

OTHER PUBLICATIONS

Halliwell, "Oxidants and human disease: some new concepts," *FASEB J.*, vol. 1, 1987, pp. 358–364.

Abstract 62–12757, Patent Abstracts of Japan, vol. 11, No. 192 (C–429)[2639], Jun. 19, 1987.

Abstract 1–213276, Patent Abstracts of Japan, vol. 13, No. 523 (C–657)[3871], Nov. 21, 1989.

Metsa–Ketela et al., "Radical–Trapping Antioxidant Properties of Nitecapone," *Digestive Diseases and Sciences*, vol. 35, No. 8, Aug. 1990.

Fujimoto et al., "Biological Antioxidant Activities of Bromophenols and Certain Other Antioxidants," *Agric. Biol. Chem.*, vol. 50, No. 1, pp. 101–108, 1986.

Suzuki et al., "Antioxidant Properties of Nitecapone (OR–462)," *Free Radical Biology & Medicine*, vol. 13, pp. 517–525, 1992.

Hearse & Tosaki, J. Mol. Cell. Cardiol. 20:213–223 (1988).

"Catechol O–methyltransferase. 10. 5–Substituted, 3–hydroxy–4–methoxybenzoic acids (isovanillic acids) and 5–substituted, 3–hydroxy–4–methoxybenzaldehydes (isovan=illins) as potential inhibitors," Borchardt, Ronald T., et al., Chemical Abstracts, vol. 96, Mar. 1982, p. 81807a.

"A useful synthesis of ethyl indole–2–carboxylates and 3,4–dihydrocarboxtyrils," Mali, R. S., et al., Chemical Abstracts, vol. 102, Apr. 1985, p. 580 (62028y).

"The effect of ring–fluorination on the rate of O–methylation of dihydroxy–phenylalanine (DOPA) by catecho=1–0–methyltransferase: significance in the development of $^{18}$F–PETT scanning agents," Creveling, Cyrus R., et al., Chemical Abstracts, vol. 104: 207624t. Aug. 1989.

"On the secondary products of the synthesis of vanillin from guaiacol and of ethylvanillin from pyrocatechol monoethyl ether; 4–hydroxy–5–methoxy–and 4–hydroxy–5–ethoxyisophthalaldehydes," Favre, Claude, Chemical Abstracts, vol. 48, Jun. 1954, p. 5831.

"Syntheses of heterocyclic compounds. CDXXXV. Nitrenes. IX. Reaction of β–(2–nitrobenzoyl)–2–nitrostyrene derivatives with triethyl phosphite," Kametani, Tetsuji, et al., Chemical Abstracts, vol. 75, p. 308 (151626h), Sep. 1971.

"Synthesis of 2,3–dimethoxy–5–methyl–p–benzoquinone," Sato, Kikumasa, et al., Chemical Abstracts, vol. 78, p. 471 (29377z), Jun. 1973.

*Primary Examiner*—Zohreh Fay
*Assistant Examiner*—Keith MacMillan
*Attorney, Agent, or Firm*—Burns, Doane, Swecker & Mathis

[57] ABSTRACT

Known and new catechol derivates may be used as medicinal antioxidants in the prevention or treatment of tissue damage induced by lipid peroxidation. The conditions and diseases to be treated are for example heart disease, rheumatoid arthritis, cancer, inflammatory disease, a rejection reaction in organ transplants, ischemia, cancer and aging.

2 Claims, No Drawings

CATECHOL DERIVATIVES, THEIR PHYSIOLOGICALLY ACCEPTABLE SALTS, ESTERS AND USE

This application is a continuation of application Ser. No. 08/294,762, filed Aug. 23, 1994, now abandoned which is a continuation of application Ser. No. 07/658,666, filed Feb. 21, 1991, now abandoned which is a continuation-in-part of U.S. Ser. No. 288,979, filed Dec. 23, 1988 now U.S. Pat. No. 5,001,152, and is a continuation-in-part of U.S. Ser. No. 587,791, filed Sep. 25, 1990 now U.S. Pat. No. 5,112,861 which is a Division of U.S. Ser. No. 126,911, filed Nov. 27, 1987 (now U.S. Pat. No. 4,963,590).

The present invention relates to catechol derivatives and their physiologically acceptable salts and esters, which are useful as medicinal antioxidants.

Medicinal antioxidants are compounds that may be used for the prevention or treatment of tissue damage induced by lipid peroxidation. Cellular damage by oxygen derived radicals especially those associated with lipid peroxidation are generally believed to be a significant factor in heart disease, rheumatoid arthritis, cancer, certain inflammatory diseases, rejection reactions in organ transplants, ischemia and even in the aging process (Halliwell, B., FASEB J. 1:358–364, 1987). During lipid peroxidation free radicals interact with polyunsaturated fatty acids to form lipid peroxyl radicals, which produce lipid hydroperoxides and further lipid peroxyl radicals. This peroxidative cascade may eventually consume essential parts of the membrane lipid, which may lead to changes in membrane permeability and ultimately in cell death. The peroxidative degradation of lipids also leads to the formation of potentially toxic products such as malondialdehyde (Comporti, M., Lab Invest. 53:599–623, 1985).

It has now been found that the catechol compounds of formula I are surprisingly effective as medicinal antioxidants

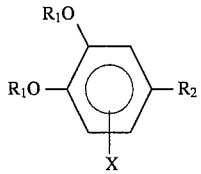

in which $R_1$ is hydrogen, X is electronegative substituent such as halogen, nitro, cyano, trifluoromethyl, formyl or carboxyl and $R_2$ is a) halogen, substituted lower alkyl, lower alkoxy, aryl or heterocyclic ring, nitro, cyano, formyl or carboxyl group or b) a group selected from

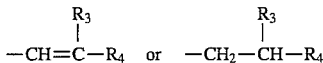

in which $R_3$ is hydrogen, lower alkyl, cyano, carboxyl, cycloalkyl carbonyl or lower acyl and $R_4$ is hydrogen, cyano, carboxyl, formyl, lower alkoxy, lower alkoxycarbonyl, lower alkoxycarbonyl lower alkyl, lower carboxy alkenyl, carboxycarbonyl, nitro, lower acyl, lower hydroxyalkyl, lower carboxyalkyl, or one of following substituted or unsubstituted groups; carbamoyl, aryl, heterocyclic ring, cycloalkyl, cycloalkyl carbonyl, aroyl, or COZ, in which Z is a substituted or unsubstituted heterocyclic ring or c)

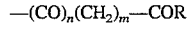

in which n is 0–1, m is 0–7 and R is lower alkyl, hydroxy, lower carboxyalkyl, substituted or unsubstituted lower alkenyl, substituted or unsubstituted heterocyclic ring or aryl, lower alkoxy or substituted or unsubstituted amino

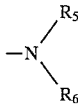

in which $R_5$ and $R_6$ independently comprise hydrogen or one of the following substituted or unsubstituted groups; lower alkyl, lower alkenyl, lower alkynyl, cycloalkyl, aralkyl or taken together with nitrogen form a substituted or unsubstituted heterocyclic ring.

Most of the above compounds are known and have been described e.g. in British Patent Application 8727854, EP-A-0323162 and in EP-A-0237929 which are herein incorporated by reference. They have been shown to be effective medicaments for treating Parkinsonism as well as in the treatment and prophylaxis of ulcers and lesions in the gastrointestinal tract.

The invention also provides new compounds of formula I, in which $R_1$ and X are the same as defined above and $R_2$ is

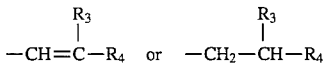

in which $R_3$ is lower acyl or cyclopropyl carbonyl and $R_4$ is substituted or unsubstituted aryl or cyclopropyl carbonyl.

Among preferred compounds according to the invention are those in which X is nitro, cyano or chloro, especially in the 5 position. In these compounds $R_2$ is especially nitro, cyano, substituted lower alkyl or a group

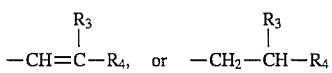

in which $R_3$ is carboxyl, cycloalkyl carbonyl or lower acyl and $R_4$ is carboxyl, lower acyl, formyl, lower alkoxycarbonyl, carboxycarbonyl, one of the following substituted or unsubstituted groups carbamoyl, cycloalkylcarbonyl, aroyl or COZ, in which Z is a substituted or unsubstituted heterocyclic ring. Preferred are also compounds of formula

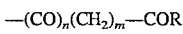

in which n is 0 and m is 0 and R is a substituted or unsubstituted amino or n is 0, m is 1 to 4 and R is lower alkyl, hydroxy, lower carboxyalkyl, a substituted or unsubstituted lower alkenyl, a substituted or unsubstituted heterocyclic ring or aryl, lower alkoxy or a substituted or unsubstituted amino.

Among these compounds may be mentioned e.g.
3-nitro-5-[2-(4-pyridyl)vinyl]catechol,
3-nitro-5-[2-(4-quinolyl)vinyl]catechol,
3,4-dihydroxy-5-nitrocinnamic acid,
3,4-dihydroxy-5-nitro-ω,ω-dicyanostyrene,
4-(3,4-dihydroxy-5-nitrophenyl)-3-methylbut-3-en-2-one,
3-(3,4-dihydroxy-5-nitrophenyl)methylene-2,4-pentanedione,
3-(3,4-dihydroxy-5-nitrophenyl)-1-phenylprop-2-en-1-one,
3-(3,4-dihydroxy-5-nitrophenyl)-1-(4-methoxyphenyl)-prop-2-en-1-one,
3-(3,4-dihydroxy-5-nitrophenyl)-1-(3,4-dimethoxyphenyl)-prop-2-en-1-one,
3-(3,4-dihydroxy-5-nitrophenyl)-1-(3,4,5-trimethoxyphenyl)-prop-2-en-1-one,
3-(3,4-dihydroxy-5-nitrophenyl)-1-(2-hydroxyphenyl)-prop-2-en-1-one, 3-(3,4-diacetoxy-5-nitrophenyl)-1-phenylprop-2-en-1-one,
3-(3,4-dibenzoyloxy-5-nitrophenyl)-1-phenylprop-2-en-1-one,
3-(3-pivaloyloxy-4-hydroxy-5-nitrophenyl)-1-phenyl-prop-2-en-1-one,
4-(3,4-dihydroxy-5-nitrophenyl)-3-methylbut-3-en-2-ol,
3',4'-dihydroxy-5'-nitroacetophenone,
5-(3,4-dihydroxy-5-nitrophenyl)pentanoic acid,
1-benzyl-4-[5-(3,4-dihydroxy-5-nitrophenyl)pentanoyl]-piperazine hydrochloride,
N-isopropyl-5-(3,4-dihydroxy-5-nitrophenyl)pentanoic amide,
N-methyl-N-propargyl-5-(3,4-dihydroxy-5-nitrophenyl)pentanoic amide,
N-(1-adamantyl)-5-(3,4-dihydroxy-5-nitrophenyl)pentanoic amide,
3-(3,4-dihydroxy-5-nitrophenyl)-1-(4-methylphenyl)-prop-2-en-1-one,
N-(1-adamantyl)-3,4-dihydroxy-5-nitrobenzamide,
4-cyclohexylcarbonyl-1-(3,4-dihydroxy-5-nitrobenzoyl)-piperidine,
N-benzyl-3,4-dihydroxy-5-nitrobenzamide,
N-(1-adamantyl)-3,4-dihydroxy-5-chlorobenzamide,
N-(1-adamantyl)-3,4-dihydroxy-5-cyanobenzamide,
1-butyl-3,4-dihydroxy-5-cyanobenzoate,
3-(3-ethoxycarbonylmethylcarbamoyloxy-4-hydroxy-5-nitrophenyl)-1-phenylprop-2-en-1-one,
3-(3,4-dihydroxy-5-nitrophenyl)-1-(2-carboxyphenyl)-prop-2-en-1-one,
3-(3,4-dihydroxy-5-nitrophenyl)-1-(4-nitrophenyl)-prop-2-en-1-one,
ethyl 2-cyano-3-(3,4-dihydroxy-5-nitrophenyl)acrylate,
methyl 3-(3,4-dihydroxy-5-nitrophenyl)methylene-4-ketopentanoate,
3,4-dihydroxy-5-nitrobenzylmalonitrile,
ethyl 3,4-dihydroxy-5-nitrobenzylcyanoacetate,
3-(3,4-dihydroxy-5-trifluoromethylphenyl)-prop-2-en-1-one,
3,4-dihydroxy-5-cyanobenzaldehyde,
3-(3,4-dihydroxy-5-trifluoromethylbenzaldehyde,
2-cyano-3-(3,4-dihydroxy-5-nitrophenyl)acrylamide,
N,N-dimethyl-2-cyano-3-(3,4-dihydroxy-5-nitrophenyl)-acrylamide,
N,N-diethyl-2-cyano-3-(3,4-dihydroxy-5-nitrophenyl)-acrylamide,
N-isopropyl-2-cyano-3-(3,4-dihydroxy-5-nitrophenyl)-acrylamide,
N'-methyl-N"-[2-cyano-3-(3,4-dihydroxy-5-nitrophenyl)-acryl]piperazine
3-(3,4-dihydroxy-5-trifluoromethylphenyl)methylene-2,4-pentanedione,
3,4-dihydroxy-5-nitrobenzylalcohol,
3,4-dihydroxy-5-nitrobenzyl-2-methoxyethyl ether,
3,4-dihydroxy-5-nitrobenzylthioacetic acid,
2-(3,4-dihydroxy-5-nitrobenzyl)pyrrole,
2-cyano-3-(3,4-dihydroxy-5-nitrophenyl)propanol,
3,5-dinitrocatechol,
3,4-dihydroxy-5-nitrobenzaldehyde,
3,4-dihydroxy-5-nitrobenzonitrile,
4-chloro-6-nitrocatechol,
4,5-dihydroxyisophtalaldehyde,
3,4-dihydroxy-5-cyanobenzoic acid,
3,5-dicyanocatechol,
N-(3-hydroxypropyl)-3,4-dihydroxy-5-nitrobenzamide,
neopentyl 2-cyano-3-(3,4-dihydroxy-5-nitrophenyl)acrylate,
N-(3-hydroxypropyl)-2-cyano-3-(3,4-dihydroxy-5-nitrophenyl)acrylamide,
5-(3,4-dihydroxy-6-nitrophenyl)pentanoic acid,
N-(1-adamantyl)-3,4-dihydroxy-6-nitrobenzamide,
N-(4-morpholine ethyl)-3,4-dihydroxy-6-nitrobenzamide-hydromesylate,
N-(1-adamantyl)-3,4-dihydroxy-6-chlorobenzamide,
1-(3,4-dihydroxy-6-nitrobenzoyl)-4-cyclohexylcarbonyl-piperidine and
1-(3,4-dihydroxy-6-nitrobenzoyl)-4-(1-piperidyl)piperidine hydromesylate. The preparation of the above compounds has been described in British Patent Application 8727854.

Also preferred compounds are N-(1-adamantyl)-3,4-dihydroxy-5-cyanobenzamide,
3,4-dihydroxy-5-nitrophenylmethanethiol,
4-[(3,4-dihydroxy-5-cyanophenyl)methylene]-3,5-heptanedione,
5-(3,4-dihydroxy-5-nitrophenyl)-2-methyl-4-phenyl-4-penten-3-one,
4-[(3,4-dihydroxy-5-cyanophenyl)methylene]-3,5-pentanedione,
1-(3,4-dihydroxy-5-nitrophenyl)-2-methylene-1-propanone,
3-(3,4-dihydroxy-5-nitrobenzyl)-2,4-pentanedione,
3-(3,4-dihydroxy-5-chlorophenyl)methylene-2,4-pentanedione,
4-(3,4-dihydroxy-5-nitrophenyl)methylene-3,5-heptanedione and
4-(3,4-dihydroxy-5-nitrobenzyl)-3,5-heptanedione, the preparation of which has been described below.

The term "alkyl" as employed herein by itself or as part of another group refers to both straight and branched carbon chain radicals. The term "lower alkyl" refers to an alkyl group of up to 7 carbon atoms, more preferably 1 to 4 carbon atoms, most preferably 1 to 2 carbon atoms.

The terms "alkenyl" and "alkynyl" as employed herein refer to an alkyl as defined above having at least one carbon to carbon double group and carbon to carbon triple bond, respectively.

The term "acyl" as employed herein refers to an alkylcarbonyl or alkenylcarbonyl group, the alkyl and alkenyl groups being defined above. The term "aryl" refers to an arylcarbonyl group, the aryl group being a monocyclic or bicyclic group containing 6 to 10 carbon atoms in the ring portion.

The term "alkoxy" as employed herein refers to an alkyl residue as defined above linked to an oxygen atom.

The term "cycloalkyl" as employed herein refers to saturated cyclic hydrocarbon groups having 3 to 10, preferably 5 to 7 carbon atoms.

The term "aralkyl" as employed herein refers to alkyl groups as defined above having an aryl substituent.

The term "heterocyclic" ring as employed herein refers to a monocyclic or bicyclic ring having 1 to 3, preferably 1 to 2 heteroatoms N and/or O and/or S. The ring may be aromatic or nonaromatic. The term "heteroaromatic" refers to aromatic heterocyclic ring. Specific examples are morpholinyl, piperidyl, piperazinyl, pyridyl, pyrrolyl and quinolyl.

The "optional substituent" as employed herein refers to halogen, trifluoromethyl, nitro, cyano, hydroxy, carboxy, lower alkyl, lower hydroxyalkyl, thiol, lower alkyl thio, lower carboxyalkyl thio, lower alkoxy, lower alkenyl, lower alkynyl, aryl, heteroaryl, lower alkyl aryl, halogen aryl, cycloalkyl, cycloalkyl carbonyl, lower alkylcycloalkyl, lower alkylamino, lower alkanoylamino, arylcarbonylamino, lower alkoxy lower alkoxy, aryl lower alkyl and alkoxy carbonyl.

For example, when $R_2$ is lower alkyl the substituents may be halogen, cyano, thiol, lower alkyl thio, lower alkoxy lower alkoxy, lower alkoxy, lower carboxyalkyl thio and heteroaryl.

When $R_4$ is optionally substituted carbamoyl the substituents may be for example lower alkyl and lower hydroxyalkyl. The optional substituents of aryl and aroyl may be halogen, trifluoromethyl, nitro, cyano, hydroxy, carboxy, lower alkyl, lower hydroxyalkyl, lower alkoxy, lower alkyl amino and those of the heterocyclic ring may be the same and further lower alkyl, aryl lower alkyl and cycloalkylcarbonyl. The optional substituents of cycloalkyl are preferably lower alkyl and halogen.

When R is optionally substituted alkenyl the substituents are preferably halogen, carboxy, alkoxy carbonyl and lower alkoxy. The optional substituents for R being a heterocyclic ring and aryl are the same as given above.

When $R_5$ and/or $R_6$ are optionally substituted lower alkyl, lower alkenyl, cycloalkyl, heterocyclic ring or aralkyl the optional substituents may be the same as given above and those of lower alkynyl the same as for lower alkenyl.

British Patent Application 8727854, EP-A-0323162 and EP-A-0237929 disclose a general method whereby the compounds according to the invention can be prepared. For example the compounds of formula I, in which $R_2$ is

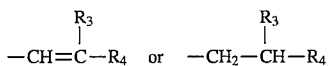

in which $R_3$ and $R_4$ are as defined above, may be prepared by condensing the compound of formula II

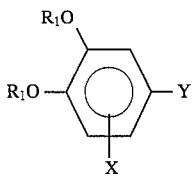

in which $R_1$ and X are as defined above, and Y is —CHO or —CH$_2$Q, in which Q is hydroxy, halogen or an alkyl or aryl sulfonate group, in the presence of acidic or basic catalyst with a compound of formula III

in which $R_3$ and $R_4$ are as defined above, giving the compounds of formula Ia and Ib, respectively,

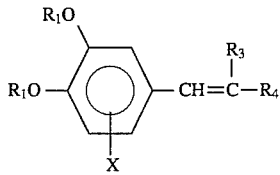

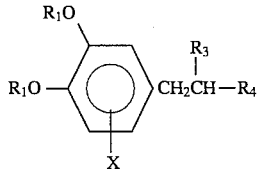

in which $R_1$, X, $R_3$ and $R_4$ are as defined above.

Alternatively, the compound of formula Ib may be prepared by reducing the double bond of the compound of formula Ia to a single bond, using the known reduction agents, for example sodium borohydride. It is also possible to prepare the compound Ia from the compound Ib by halogenating the compound of formula Ib to give the compound of formula IV

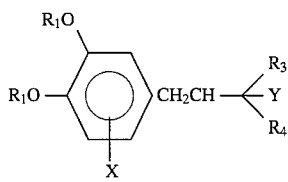

in which $R_1$, X, $R_3$ and $R_4$ are as defined above and Y is halogen and dehydrohalogenating compound IV to produce a compound of formula Ia.

Methods for the preparation of esters of the compounds according to the invention have been described in the above mentioned patent applications. Preferred esters are lower acyl, lower alkyl carbamoyl or aroyl derivatives which will hydrolyze readily under physiological conditions.

Salts of these compounds, when applicable, may be prepared by known methods. All physiologically acceptable salts are useful as active medicaments, however, preferred are sodium, potassium, ammonium, calcium and magnesium salts and salts with hydrochloric, hydrobromic, phosphoric and sulfuric acids and with the organic acids like oxalic, fumaric, tartaric, malonic, acetic and citric acids etc.

The effective dose of the compound varies considerably depending on whether the compounds are given for prophylaxis or for treatment, the severity of the condition to be treated, and the route of administration. The effective dose for human beings is likely to be from about 1 to 1000 mg per day.

The compounds used in this invention are formulated into dosage forms using the principles which are known to the man having average skill in the art. The compounds according to this invention are given to a patient as such or in combination with suitable pharmaceutical material in the form of tablets, dragees, capsules, suppositories, emulsions, suspensions or solutions whereby the contents of the active compound is in the formulation from 1 to 100 weight %.

Choosing the auxiliary ingredients for the formulation is routine for those of ordinary skill in the art. It is evident that suitable solvents, gel forming ingredients, dispersion forming ingredients, colors etc. are used in a normal way.

The compositions may be administered enterally or parenterally.

Test Results

Radical Trapping Capacity of Compounds

The tested compounds were subjected to controlled peroxidation by peroxyl radicals originating from the thermal decomposition of 2,2'-azobis-(2-amidinopropane)*2HCl at 37° C. The rate of radical formation was followed by luminol enhanced chemiluminescence (CL). From the duration of CL and from the fact that the phenolic antioxidant vitamin E analogue TROLOX® traps two radicals (Barclay, L. et al., J. Am. Chem. Soc. 106: 2479–2481, 1984) the stoichiometric factors were calculated. The results are presented in Table 1.

TABLE 1

The binding of peroxyl radicals by various test compounds

| Compound | Stoichiometric Factor |
|---|---|
| 1 | 5.5 |
| 2 | 5.0 |
| 3 | 4.0 |

TABLE 1-continued

The binding of peroxyl radicals by various test compounds

| Compound | Stoichiometric Factor |
|---|---|
| 4 | 3.9 |
| 5 | 3.6 |
| 6 | 3.5 |
| 7 | 3.3 |
| 8 | 3.2 |
| 9 | 3.0 |
| 10 | 2.6 |
| 11 | 2.6 |
| 12 | 2.4 |
| 13 | 2.3 |
| 14 | 2.1 |
| TROLOX | 2.0 |
| Ascorbic acid | 0.7 |

1 3-(3,4-dihydroxy-5-nitrobenzyl)-2,4-pentanedione
2 3-(3,4-dihydroxy-5-nitrophenyl)methylene-2,4-pentanedione
3 3-(3,4-dihydroxy-5-chlorophenyl)methylene-2,4-pentanedione
4 N-(1-adamantyl)-3,4-dihydroxy-5-cyanobenzamide
5 3,4-dihydroxy-5-nitrophenylmethanethiol
6 4-[(3,4-dihydroxy-5-cyanophenyl)methylene]-3,5-heptane-dione
7 5-(3,4-dihydroxy-5-nitrophenyl)-2-methyl-4-phenyl-4-penten-3-one
8 3,5-dicyanocatechol
9 3,5-dinitrocatechol
10 4-[(3,4-dihydroxy-5-cyanophenyl)methylene]-3,5-pentane-dione
11 1-(3,4-dihydroxy-5-nitrophenyl)-2-methylene-1-propanone
12 N,N-diethyl-2-cyano-3-(3,4-dihydroxy-5-nitrophenyl)-acrylamide
13 3,4-dihydroxy-2'-fluoro-5-nitrobenzophenone
14 3,4-dihydroxy-4'-methyl-5-nitrobenzophenone The total peroxyl radical trapping antioxidant parameter (TRAP) for the test compound 1 was studied in vivo by dosing 1 mg/kg or 10 mg/kg i.v. to rats. Plasma samples were taken at 0, 5, 15, 30 and 60 min after dosing. The plasma TRAP was calculated as μM of trapped radicals.

TABLE 2

Plasma TRAP (μM) after i.v. dosing of the test compound 2

| Group | Plasma TRAP (μM) | | | | |
|---|---|---|---|---|---|
| | 0 min | 5 min | 15 min | 30 min | 60 min |
| 1 mg/kg | 294 | 315 | 324 | 320 | 304 |
| 10 mg/kg | 263 | 867 | 584 | 461 | 309 |
| control | 251 | 211 | 226 | 210 | 231 |

Control = not treated
n = 9 per group

The following examples illustrate the production of compounds of use according to the invention.

EXAMPLE 1

4-(3,4-Dihydroxy-5-nitrophenyl)-3-phenyl-3-buten-2-one

A solution containing 2.68 g of 3-phenyl-2-propanone and 3.66 g of 3,4-dihydroxy-5-nitrobenzaldehyde in 80 ml of 2-propanol was saturated with hydrogen chloride gas at 20° C. The mixture was stirred for 4 h at room temperature, filtered and washed with 2-propanol. The product was recrystallized from methanol. Yield 1.34 g, mp 170°–176° C.

EXAMPLE 2

4-(3,4-Dihydroxy-5-nitrophenyl)-3-(4-methylphenyl)-3-buten-2-one

The procedure described in Example 1 was repeated by using 0.81 g of 3-(4-methylphenyl)-2-propanone and 0.92 g of 3,4-dihydroxy-5-nitrobenzaldehyde. Yield 0.82 g, mp 189°–194° C.

EXAMPLE 3

5-(3,4-Dihydroxy-5-nitrophenyl)-2-methyl-4-phenyl-4-penten-3-one

The procedure described in Example 1 was repeated by using 2.96 g of 2-methyl-4-phenyl-3-butanone and 2.4 g of 3,4-dihydroxy-5-nitrobenzaldehyde. Yield 0.52 g, mp 151°–156° C.

EXAMPLE 4

3-(3,4-Dihydroxy-5-nitrobenzyl)-2,4-pentanedione

A mixture containing 6.0 g of 3,4-dihydroxy-5-nitrobenzyl-alcohol and 1.0 ml of trifluoroacetic acid in 70 ml of 2,4-pentanedione was heated for 20 h at 100° C. The solvents were evaporated in vacuo and the residue was crystallized from 2-propanol. Yield 3.0 g, mp 118°–128° C.

EXAMPLE 5

3-[(3,4-Dihydroxy-5-chlorophenyl)methylene]-2,4-pentanedione

A mixture containing 3.45 g of 3,4-dihydroxy-5-chlorobenzaidehyde, 3.0 ml of 2,4-pentanedione, 0.3 ml of piperidine and 1.0 ml of acetic acid in 100 ml of 1-butyl acetate was refluxed for 2 h with Dean-Stark separator. The solution was filtered and the solvent was evaporated in vacuo. The residue was crystallized from 1-propanol. Yield 0.46 g, mp 167°–171° C.

EXAMPLE 6

4-[(3,4-Dihydroxy-5-cyanophenyl)methylene]-3,5-heptanedione

A mixture 1.6 g of 3,4-dihydroxy-5-cyanobenzalde, 2.5 g of 3,5-heptanedione, 0.2 ml of piperidine and 0.6 ml of acetic acid in 70 ml of toluene was refluxed for 2 h with Dean-Stark separator. The solvent was evaporated in vacuo and the residue was crystallized from acetone-cyclohexane. Yield 0.33 g, mp 165°–173° C.

EXAMPLE 7

1,3-Dicyclopropyl-2-[(3,4-dihydroxy-5-nitrophenyl)methylene]-1,3-propanedione

A mixture containing 2.75 g of 3,4-dihydroxy-5-nitrobenzaldehyde, 3.8 g of 1,3-dicyclopropyl-1,3-propanedione, 0.2 ml of piperidine and 0.4 ml of acetic acid was refluxed for 1 h with a Dean-Stark separator. After cooling the product was filtered and recrystallized from acetic acid. Yield 2.85 g, mp 159°–162° C.

EXAMPLE 8

3,4-Dihydroxy-5-nitrophenyl methanethiol a) 3,4-Dihydroxy-5-nitrobenzyl bromide 12.2 g of 3,4-dihydroxy-5-nitrobenzyl alcohol was dissolved in 100 ml of 47% hydrobromic acid at 50° C. After cooling the product was filtered and washed with 47% hydrobromic acid. The crude product was dissolved in dichloromethane and dried over $Na_2SO_4$. The mixture was filtered and the solvent was evaporated in vacuo. Yield 7.1 g.

b) 3,4-Dihydroxy-5-nitrophenylmethanethiol 2.5 g of the above product was gradually added to a solution containing 3.0 g of sodium hydrogen sulfide in 30 ml of N-methylpyrrolidone and 20 ml of water. The solution was stirred for 45 min at 20° C. 100 ml 1N hydrochloric acid was then added and the solution was extracted twice with 100 ml of ether. The ether extract was washed with conc. $Na_2SO_4$-solution, dried over $Na_2SO_4$. After filtering the solvent was evaporated in vacuo and the residue was crystallized from water. Yield 0.35 g, mp 179°–185° C.

EXAMPLE 9

N-(1-Adamantyl)-3,4-dihydroxy-5-cyanobenzamide a) N-(1-Adamantyl)-3,4-diacetoxy-5-cyanobenzamide A solution containing 0.8 g of 3,4-diacetoxy-5-cyanobenzoic acid and 0.32 ml of thionyl chloride and a catalytic amount of N,N-dimethylformamide in 10 ml of toluene was heated for 1 h at 80° C. The solvent was evaporated in vacuo and the residue was dissolved in 5 ml of dichloromethane and added to a mixture containing 0.56 g of 1-aminoadamantane hydrochloride and 0.94 ml of triethylamine in 10 ml of dichloromethane and stirred for 15 min at 0° C. and then 15 min at 20° C. water was added to the reaction mixture and dichloromethane phase was separated. The solvent was evaporated in vacuo yielding yellow viscous oil 1.0 g.

b) N-(1-Adamantyl)-3,4-dihydroxy-5-cyanobenzamide

A solution containing 1.2 g of the above product and a catalytic amount of sulfuric acid in 10 ml of methanol was refluxed for 3 h. 20 ml of water was added and on cooling 0.75 g of the desired product was crystallized, m.p. 253°–255° C.

EXAMPLE 10

4-[(3,4-Dihydroxy-5-cyanophenyl)methylene]-3,5-pentanedione

A mixture 1.6 g of 3,4-dihydroxy-5-cyanobenzaldehyde, 2.0 g of 3,5-pentanedione, 0.2 ml of piperidine and 0.6 ml of acetic acid in 70 ml of toluene was refluxed for 2 h with Dean-Stark separator. The solvent was evaporated in vacuo and the residue was crystallized from acetone-cyclohexane. mp 228°–232° C.

EXAMPLE 11

1-(3,4-Dihydroxy-5-nitrophenyl)-2-methylene-1-propanone a) 3',4'-Dimethoxy-2-bromoisobutyrophenone A mixture of veratrole (1,3-dimethoxybenzene) (13.8 g), 2-bromoisobutyryl bromide (23.0 g) and aluminium chloride (14.0 g) was heated for 1 hour at 70°–80° C. After cooling, ice and hydrochloric acid were added to the reaction mixture which was then extracted with ether. The extract was washed first with water and then with 1N NaOH-solution, dried and the solvent evaporated in vacuo, yielding a pale yellow oil (12.3 g).

b) 4'-Hydroxy-3'-methoxy-2-bromoisobutyrophenone

A solution of 3',4'-dimethoxy-2-bromoisobutyrophenone (11.5 g) and aluminium bromide (21.8 g) in toluene (220 ml) was refluxed for 15 min. After cooling the reaction mixture was poured into ice (300 g) and 1N hydrochloric acid (200 ml). The organic phase was separated and dried over $Na_2SO_4$. The solvent was evaporated in vacuo yielding a pale yellow oil (10.0 g).

c) 4'-Hydroxy-3'-methoxy-5'-nitro-2-bromoisobutyrophenone

To a solution of 4'-hydroxy-3'-methoxy-2-bromoisobutyrophenone (10.0 g) in dichloromethane (80 ml) was gradually added 2M $HNO_3$-dichloromethane (19 ml). The mixture was stirred for 2 hours at 10° C. after which water (100 ml) was added. The organic phase was separated, dried over $Na_2SO_4$ and evaporated to dryness. Ether (20 ml) was added. The resulting crystals were filtered and washed with ether. Yield 3.3 g.

d) 3',4'-Dihydroxy-5'nitro-2-bromoisobutyrophenone

To a solution of 4'-dihydroxy-3'-methoxy-5'-nitro-2-bromoisobutyrophenone (3.0 g) in dichloromethane (60 ml) was gradually added 1M $BBr_3$-dichloromethane (30 ml). The solution was stirred over night at room temperature. Water and hydrochloric acid were added to the reaction mixture. The organic phase was separated and evaporated to dryness. Yield 2.6g.

e) 1-(3,4-Dihydroxy-5-nitrophenyl)-2-methylene-1-propanone

A solution of 3',4'-dihydroxy-5'-nitro-2-bromoisobutyrophenone (2.6 g) and triethylamine (20 ml) in pyridine (20 ml) was heated for 3 hours at 100° C. Triethylamine and pyridine were evaporated in vacuo. Ether and 2N $H_2SO_4$ were added. The organic phase was separated and dried over $Na_2SO_4$. The ether solution was treated with charcoal for 2 hours, filtered and evaporated to dryness. The residue was crystallized from dichloromethane-petroleum ether (40°–60° C). Yield 0.48 g, mp 98°–102° C.

EXAMPLE 12

4-(3,4-Dihydroxy-5-nitrophenyl)methylene-3,5-heptanedione

To a solution of 3,4-dihydroxy-5-nitrobenzaldehyde (7.6 g) and 3,5-heptanedione (8.0 g) in 50 ml of 2-propanol was added thionyl cloride (3.5 ml) with stirring at 20° C. Ether (60 ml) was added and the solution was filtered and allowed to stand overnight. The resulting crystal were filtered. Yield 1.2 g, mp 133°–135° C.

EXAMPLE 13

4-(3,4-Dihydroxy-5-nitrobenzyl)-3,5-heptanedione.

A mixture containing 0.2 g of 3,4-dihydroxy-5-nitrobenzyl alcohol and 0.03 ml of trifluoroacetic acid in 2.5 ml of 3,4-heptanedione was heated for 20 h at 100° C. The solvent was evaporated in vacuo and the residue was recrystallized from 2-propanol. Yield 0.3 g, mp 126°–131° C.

EXAMPLE 14

2-(3,4-Dihydroxy-5-nitrobenzyl)-1-cyclopropyl-1,3-butanedione

The procedure described in Example 4 was repeated by using 0.18 g of 3,4-dihydroxynitrobenzyl alcohol and 2 ml of 1-cyclopropyl-1,3-butanedione. The residue was crystallized from diethylether. Yield 52 mg, mp 98°–104° C.

We claim:

1. A method for the prevention or treatment of tissue damage induced by lipid peroxidation associated with ischemia by administering to a patient in need of such prevention or treatment an effective amount to prevent or treat tissue damage induced by lipid peroxidation of the compound of formula I

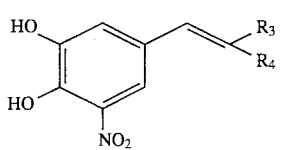
wherein R₃ is cyano or lower acyl and R₄ is lower acyl or carbamoyl which is unsubstituted or substituted by lower alkyl or lower hydroxyalkyl or a physiologically acceptable salt or ester thereof.
2. The method according to claim 1, in which the compound is 3-(3,4-dihydroxy-5-nitrophenyl)methylene-2,4-pentanedione.
* * * * *